US00PP34434P2

(12) United States Plant Patent
Hansen

(10) Patent No.: US PP34,434 P2
(45) Date of Patent: Jul. 19, 2022

(54) ***MONARDA* PLANT NAMED 'PARDON MY ROSE'**

(50) Latin Name: *Monarda didyma*
Varietal Denomination: 'Pardon My Rose'

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/300,867

(22) Filed: Nov. 29, 2021

(51) Int. Cl.
*A01H 5/02* (2018.01)
*A01H 6/50* (2018.01)

(52) U.S. Cl.
USPC ..... Plt./455
CPC ..... *A01H 6/50* (2018.05)

(58) Field of Classification Search
USPC ..... Plt./455
CPC ..... A01H 6/50
See application file for complete search history.

*Primary Examiner* — Anne Marie Grunberg

(57) ABSTRACT

The new and distinct cultivar of ornamental cultivar of bee balm plant named *Monarda didyma* 'Pardon My Rose' has short, compact, basally branching stems, dark green foliage with strong resistance to powdery mildew and numerous large flower heads of intense rose-pink-colored flowers creating excellent flower coverage. The new plant is attractive and useful in the garden landscape as a specimen, en masse, or as a container plant.

1 Drawing Sheet

Botanical classification: *Monarda didyma.*
Variety denomination: 'Pardon My Rose'.

STATEMENT REGARDING PRIOR DISCLOSURES UNDER 37 CFR 1.77(b)(6)

The first non-enabling disclosure of the claimed plant was made on Dec. 1, 2020 in the form of photograph and brief description on a website operated by Walters Gardens, Inc., followed on May 21, 2021 by a photograph and brief description in the "Walters Gardens 2021-2022 Catalog." Walters Gardens, Inc obtained the plant and all information relating thereto, from the inventor. The first sales of the new plant were on May 3, 2021 by Walters Gardens, Inc. to Bachman's Nursery, Inc. No plants of *Monarda* 'Pardon My Rose' have been sold, in this country or anywhere in the world, nor has any disclosure of the new plant been made more than one year prior to the filing date of this application, and such sale or disclosure within one year was either derived directly or indirectly from the inventor.

BACKGROUND OF THE INVENTION

The present invention relates to the new and distinct cultivar of bee balm plant, botanically known as *Monarda didyma* 'Pardon My Rose', and hereinafter also referred to solely as the cultivar 'Pardon My Rose' or the "new plant". The new plant was selected from self-pollination on Jun. 17, 2015 from an unreleased, proprietary hybrid known only by the hybridizer code 14-47-1 in a designated hybridizing plot of a wholesale perennial nursery in Zeeland, Mich., USA. The new plant was a single seedling selection originally made in the summer of 2017 from the seeds that were sown in the fall of 2015 and the plant was assigned the breeder code of 15-34-10. Further selection was completed in the trial fields of a wholesale perennial nursery in Zeeland, Mich. in the summer of 2019.

The new plant has been asexually propagated by shoot tip cuttings originally in 2018 at the same nursery in the greenhouses in Zeeland, Mich., and the subsequent asexually propagated plants found to be stable, true to type and identical to the original selection.

BRIEF SUMMARY OF THE PLANT

*Monarda didyma* 'Pardon My Rose' is unique from its parents and all other Bee Balm plants known to the inventors. The nearest comparison varieties are: 'Pardon My Cerise' U.S. Plant Pat. No. 29,234, 'Berry Taffy' U.S. Plant patent application Ser. No. 17/300,434, 'Cherry Pops' U.S. Plant Pat. No. 27,618, and 'Fire Marshall' U.S. Plant Pat. No. 23,286. 'Pardon My Cerise' has a similar habit with flowers that are a deep cherry-red. 'Berry Taffy' has a more compact shorter habit with flowers that are hot raspberry-pink. 'Cherry Pops' has a slightly taller habit with flowers that are cherry-red. 'Fire Marshall' has a taller habit with flowers that are deeper red.

'Petite Delight' U.S. Plant Pat. No. 10,784 is slightly shorter than the new plant and the flowers are smaller and more purplish-red. 'AChall' U.S. Plant Pat. No. 19,582 is slightly shorter than the new plant, has flowers that are much darker purplish-red. Both 'Petite Delight' and 'AChall' showed some sensitivity to powdery mildew.

The parent plant has a taller habit and the flower color is more purplish color and less reddish.

The following are traits of *Monarda didyma* 'Pardon My Rose' that in combination distinguish it from all other bee balm known to the inventor:

1. Short, winter-hardy, compact, vigorous, clumping habit;
2. Dark-green leaves that are strongly resistant to powdery mildew;

3. Large flower heads of intense, rose-pink-colored flowers for a long period in summer with excellent flower coverage;
4. Flowers are subtended by burgundy-colored bracts.

BRIEF DESCRIPTION OF THE DRAWINGS

The photographs of the new plant demonstrate the unique traits of 'Pardon My Rose' and the overall appearance of the plant at three-years old in the full sun trial garden of a wholesale perennial nursery in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
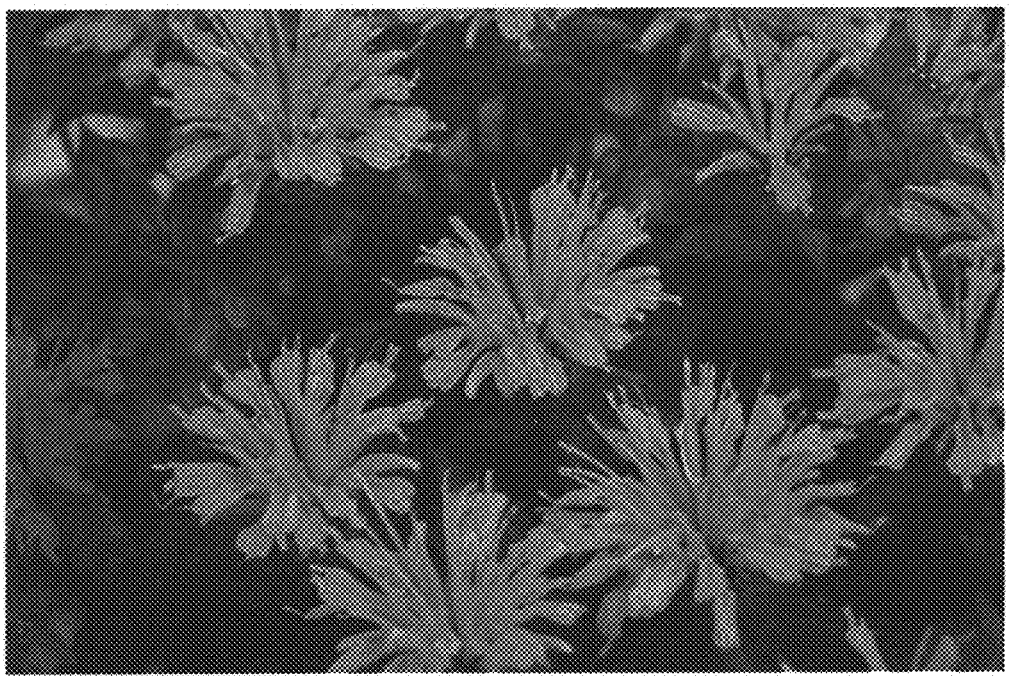
FIG. 1 shows a close-up of the flowers.
Figure 2:
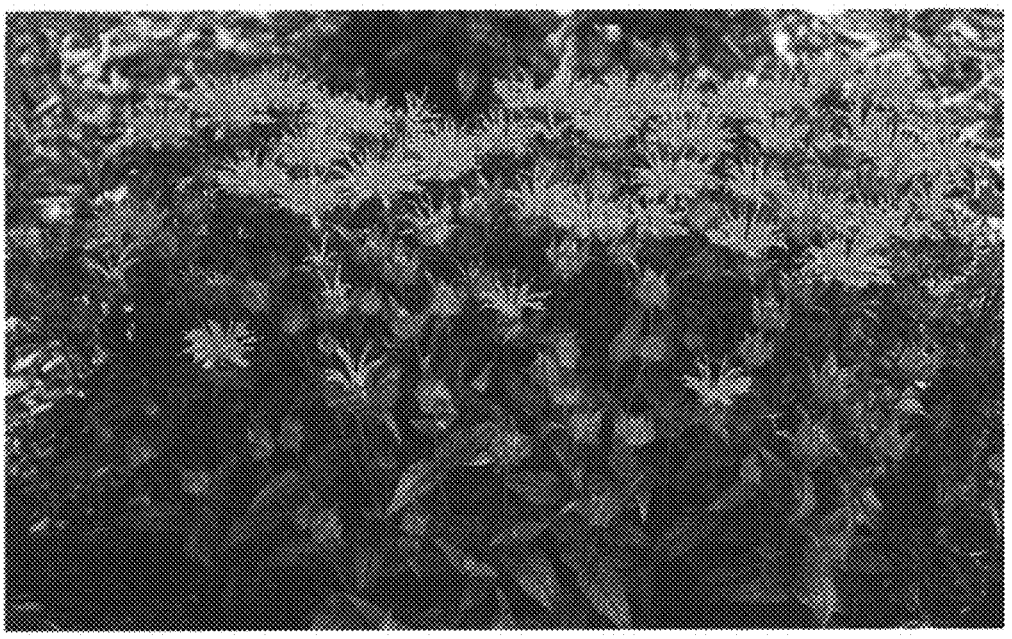
FIG. 2 shows the new plant in flower in the landscape.

The following descriptions and color references are based on the 2015 edition of The Royal Horticultural Society Colour Chart except where common dictionary terms are used. *Monarda didyma* 'Pardon My Rose' has not been observed under all possible environments. The phenotype may vary slightly with different growing environments such as temperature, light, fertility, soil pH, moisture and maturity levels, but without any change in the genotype. The following observations and size descriptions are based on three-year old greenhouse-grown plants in gallon containers at a nursery in Zeeland, Mich. with supplemental fertilizer and water as needed but without plant growth regulators or pinching.

Botanical classification: *Monarda didyma;*

Parentage: The parent is the proprietary hybrid known only as 14-47-1;

Plant habit: Winter-hardy herbaceous perennial, compact, producing several stems spreading by short rhizomes; to 40 cm tall at flowering and 70 to 80 cm wide; flowering begins mid-summer in Michigan and continuing for about 5 to 8 weeks;

Propagation: Stem cuttings;

Time to produce finished crop in 3.8-liter pots: About 8 to 10 weeks; vigorous rate of growth;

Root: Fine, fibrous and freely branching; color creamy white to tan depending on soil type;

Leaves: Simple, lanceolate, opposite, serrated, puberulent above and below; lustrous above, matte below; acute apex, rounded to cordate base; to about 6.5 cm long and about 3.5 cm wide, decreasing distally, average about 6.0 cm long and 3.0 cm wide;

Leaf color: Young expanding leaves nearest RHS 138B on adaxial surface and on abaxial surface nearest RHS 138D; mature adaxial leaves between RHS 139A and RHS 136A and abaxial leaves nearest RHS 144A;

Foliage fragrance: Pleasantly herbal;

Veins: Pinnate; pubescent below with minute puberulent above, slightly sunken above and raised below;

Vein color: Mature adaxial midrib and primary veins between RHS 145A and RHS 146D, secondary adaxial veins between RHS 139A and RHS 136A; mature abaxial midrib and primary veins between RHS 145D and RHS 145C, secondary abaxial veins nearest RHS 145B; emerging adaxial midrib and primary veins nearest RHS 138C, secondary veins on emerging abaxial surfaces same color as surrounding leaf tissue; emerging abaxial midrib and primary veins nearest RHS 145D, secondary veins nearest RHS 145B;

Petiole: Puberulent, slightly concavo-convex; to about 4.5 mm long and 2.5 mm across, decreasing distally;

Petiole color: Nearest RHS 138D with slight anthocyanin blush of nearest RHS N187A adaxial, nearest RHS 138D abaxial;

Stems: Quadrangular, puberulent, to about 4.0 mm across at base and about 37 cm long;

Stem color: Basal portion between RHS 146C and RHS 138B, distal portion in higher sun exposure nearest RHS 146B with light to moderate anthocyanin blush of nearest RHS 187A with the greater blush in regions of higher sun exposure;

Branches: In lower nodes; quadrangular, puberulent, typically three to four per main stem at initial flowering; about 2.0 mm across at base and to about 30 cm long;

Branch color: Proximally between RHS 145A and RHS 14 with moderate to light anthocyanin blush of nearest RHS 187A with greater sun exposure;

Nodes: About 12 to 16 per stem;

Node color: Nearest RHS 145A with thin bands of nearest RHS 187A above and below when exposed to high sun level;

Flowers: Single, labiate, actinomorphic flowers arranged in terminal verticillate head about 68.0 mm across and 40.0 mm tall, opening from the center and progressing outwardly and downwardly; individual flowers to about 37.0 mm long to exserted anthers; corolla to about 36.0 mm long, 15.0 mm tall and 5.0 mm across; numerous, about 80 to 120 flowers per head; flower altitude upright in center of head to outwardly toward the perimeter, slightly arcuate distally; self-cleaning;

Flower lasting: Individual flowers persisting about 5 days in Michigan, head remains effective for 2 to 3 weeks;

Flower period: Usually late June into August; about six to seven weeks;

Flower fragrance: None observed;

Buds one to two days prior to opening: Narrowly oblanceolate; tubular; rounded apex; arcuate slightly downward in distal half; about 24.0 mm long, about 3.0 mm across in the middle and about 5.0 mm tall;

Bud color one to two days prior to opening: Between RHS 63B and RHS 63C;

Petals: Bilabiate; arcuate downward; fused in proximal 12.0 mm, split in two in about the distal 15.0 mm; puberulent abaxial and glabrous adaxial except pubescent in center 3 to 5 mm of lower lip;

Upper labium: Folded into a hood about 14.0 mm long from fusion and 2.5 mm across and 3.0 mm tall just beyond fusion;

Lower labium: About 15.0 mm long beyond fusion, comprising three lobes including two side lobes about 1.0 mm long and 2.0 mm across having rounded apex entire margin, and center lobe to about 5.0 mm long and 2.0 mm wide, bent upwardly at base, with emarginate apex split in the distal 1.0 mm and entire margin;

Petal color: Basal 4.0 mm of corolla tube nearest RHS N155C both adaxial and abaxial; upper labium adaxial between RHS 63B and RHS 63C, abaxial nearest RHS 63A; lower labium adaxial between RHS 63B and RHS 63C with spots of between RHS 63B and RHS 63A, abaxial between RHS 63B and RHS 63C, distal 1.0 mm of center lobe nearest RHS 69C both adaxial and abaxial; outer corolla tube adaxial nearest RHS 63C, and abaxial nearest RHS 63B;

Floral bracts: Two sets of between 5 and 7 subtending flower head; proximal set deltoid to lanceolate, with acuminate to narrowly acute apex and sessile truncate base, to about 29.0 mm long and 10.0 mm wide; distal set lanceolate with narrowly acute apex and sessile truncate base, to about 12.0 mm long and 3.0 mm wide near base;

Floral bract color: Variable; both sets abaxial and adaxial between RHS 187A and RHS 187B and both sets adaxial and abaxial nearest RHS 146B with variable amount of anthocyanin in the center of nearest RHS 187B;

Androecium: Two;

*Filaments*.—Two, to about 36.0 mm long by 0.3 mm diameter; color proximally nearest RHS 69B, distally lighter than RHS 69D.

*Anther*.—Oblong elliptic, dorsifixed, longitudinal; 3.0 mm by 1.0 mm; color nearest RHS N77A.

*Pollen*.—Abundant, elliptic to globose, less than 0.1 mm; color nearest RHS 18D.

Gynoecium: One per flower; about 37.0 mm long at maturity, exserted;

*Style*.—About 34.0 mm by 0.3 mm; color proximally nearest RHS 69B, distally lighter than RHS 69D.

*Stigma*.—Split in two in the distal 2.0 mm, 0.2 mm in diameter; color nearest RHS 69D.

*Ovary*.—1.0 mm by 0.75 mm; color between RHS 143D and RHS 144B.

*Calyx*.—Tubular to campanulate, consisting of five fused sepals; about 9.0 mm long and 2.0 mm diameter at apex.

Sepals: Five; apiculate apex; basal 7.0 mm fused forming corolla tube; about 9.0 mm long and 1.0 mm across at fusion; glabrous adaxial and abaxial;

Sepal color: Adaxial and abaxial distally nearest RHS N186C; adaxial proximally nearest RHS 138C, abaxial proximally nearest RHS 138C with slight tinting of RHS N186C and darker veins of nearest RHS 138A;

Peduncle: Pubescent, stiff, strong, erect, quadrangular to about 0.3 cm across just above last leaves and to about 85.0 mm long;

Peduncle color: Variable depending on sun exposure; between RHS 138B and RHS 138C in low sun exposure, nearest RHS 146B with light to moderate anthocyanin blush of nearest RHS 187A in high sun exposure;

Fruit: Single nutlet, elliptical, about 1.0 mm long and 0.7 mm wide;

Hardiness: The new plant grows best with plenty of moisture and adequate drainage; hardy to at least from USDA zone 4 through 8;

Disease and pest resistance: Demonstrated strong powdery mildew resistance (*Sphaerotheca pannosa* var. *rosa*) in side-by-side comparison at least equal or better than that of 'Petite Delight' and 'AChall'.

I claim:

1. A new and distinct cultivar of ornamental bee balm plant named *Monarda* 'Pardon My Rose', as herein described and illustrated.

* * * * *